(12) United States Patent
Leeflang et al.

(10) Patent No.: US 11,305,092 B2
(45) Date of Patent: Apr. 19, 2022

(54) CATHETER DEVICES AND METHODS FOR MAKING THEM

(71) Applicant: CLPH, LLC, Palo Alto, CA (US)

(72) Inventors: Stephen A. Leeflang, Sunnyvale, CA (US); Christian S. Eversull, Palo Alto, CA (US)

(73) Assignee: CLPH, LLC., Palo Alto, CA (US)

( * ) Notice: Subject to any disclaimer, the term of this patent is extended or adjusted under 35 U.S.C. 154(b) by 526 days.

(21) Appl. No.: 16/011,398

(22) Filed: Jun. 18, 2018

(65) Prior Publication Data

US 2018/0361112 A1 Dec. 20, 2018

Related U.S. Application Data

(63) Continuation of application No. 14/932,763, filed on Nov. 4, 2015, now Pat. No. 9,999,745.

(60) Provisional application No. 62/137,817, filed on Mar. 25, 2015, provisional application No. 62/075,755, filed on Nov. 5, 2014.

(51) Int. Cl.
| | |
|---|---|
| *A61M 25/00* | (2006.01) |
| *A61B 5/042* | (2006.01) |
| *A61B 5/00* | (2006.01) |
| *D04C 3/48* | (2006.01) |
| *A61B 5/287* | (2021.01) |

(52) U.S. Cl.
CPC ...... *A61M 25/0012* (2013.01); *A61M 25/005* (2013.01); *A61B 5/287* (2021.01); *A61B 5/6852* (2013.01); *A61B 2562/0215* (2017.08); *D04C 3/48* (2013.01)

(58) Field of Classification Search
CPC ............ A61M 25/0012; A61M 25/005; A61M 25/0105; A61M 25/0133; A61M 25/0136; A61B 5/0422; A61B 18/14; A61B 2562/0215
See application file for complete search history.

(56) References Cited

U.S. PATENT DOCUMENTS

| | | | | |
|---|---|---|---|---|
| 5,057,092 A | * | 10/1991 | Webster, Jr. | ........ A61M 25/005 |
| | | | | 604/527 |
| 6,213,995 B1 | * | 4/2001 | Steen | ..................... A61B 18/14 |
| | | | | 604/527 |

(Continued)

*Primary Examiner* — Nathan R Price
*Assistant Examiner* — Justin L Zamory
(74) *Attorney, Agent, or Firm* — William A. English; Vista IP Law Group LLP

(57) ABSTRACT

Tubular devices are provided that include a proximal end, a distal end sized for introduction into a patient's body, a central lumen, a conductor extending between the proximal and distal ends adjacent the central lumen, reinforcement members including windings extending helically around the central lumen, and an outer jacket. The tubular device includes a first portion in which the conductor extends helically around the central lumen, and a second portion in which the conductor extends longitudinally and either a) all of the windings surround the central lumen and the conductor remains outside the windings, b) at least some of the windings pass between the central lumen and the conductor and at least some of the windings surround both the central lumen and the conductor, and c) all of the windings surround both the central lumen and the conductor. Methods for making such tubular devices are also provided.

21 Claims, 10 Drawing Sheets

(56) References Cited

U.S. PATENT DOCUMENTS

| | | | |
|---|---|---|---|
| 6,926,669 B1* | 8/2005 | Stewart | A61B 18/1492 600/437 |
| 2003/0009095 A1* | 1/2003 | Skarda | C22C 14/00 600/374 |
| 2004/0122360 A1* | 6/2004 | Waldhauser | A61M 25/005 604/95.04 |
| 2008/0147155 A1* | 6/2008 | Swoyer | A61N 1/05 607/116 |

* cited by examiner

CATHETER DEVICES AND METHODS FOR MAKING THEM

RELATED APPLICATION DATA

This application is a continuation of co-pending application Ser. No. 14/932,763, filed Nov. 4, 2015, issuing as U.S. Pat. No. 9,999,745, which claims benefit of provisional application Ser. Nos. 62/075,755, filed Nov. 5, 2014, and 62/137,817, filed Mar. 25, 2015, the entire disclosures of which are expressly incorporated by reference herein.

FIELD OF THE INVENTION

The present invention relates generally to reinforced catheters, sheaths, or other tubular devices including multiple lumens, and, more particularly, to catheters, sheaths, or other tubular devices including wires or other conductors braided or otherwise incorporated into the tubular devices, e.g., for electrodes, sensing elements, and/or other electrical elements carried by the tubular devices, and to methods for making such tubular devices.

BACKGROUND

Elongate tubular devices, such as diagnostic or treatment catheters or sheaths may be provided for introduction into a patient's body, e.g., the patient's vasculature or other body lumens. For example, a catheter may have a distal portion configured to be introduced into a body lumen and advanced to one or more desired locations within the patient's body by manipulating a proximal end of the catheter.

To facilitate introduction of such a catheter, one or more wires, cables, or other steering elements may be provided within the catheter, e.g., that are coupled to the distal portion and may be pulled or advanced from the proximal end to deflect the distal portion. For example, a steering element may be provided that is intended to deflect the distal portion within a predetermined plane and/or into a desired curved shape.

Pull wires are a common way to impart deflection ability to such a catheter. However, there are a number of drawbacks associated with such pull wires. For example, a pull wire occupies a significant amount of space within the catheter body. In addition, a pull wire frequently needs to be reinforced, e.g., on the inside and outside of the braid or other reinforcement of the catheter, e.g., to prevent "pull through" when the pull wire is actuated by pushing or pulling, i.e., the resulting bending moment may cause the pull wire to separate layers of or tear at least partially through the wall of catheter, potentially splitting the catheter. Further, a pull wire can make the torque properties of the catheter non-homogenous, making it difficult or impossible to torque the catheter when the pull wire is actuated, e.g., within a tortuous pathway. Further, auxiliary lumens, in particular those located in the wall of a large bore sheath, are difficult to manufacture with consistency due to difficulties with alignment, hand assembly, and the like.

In addition, catheters, sheaths, or other tubular devices may include one or more wires or conductors therein, e.g., for operating one or more elements on a distal portion of the device. Incorporating electrically conductive wires or elements into thin walled tubular devices, such as deflectable sheaths, may be challenging. For example, one or more wires may be provided inside the wall of a catheter that extend longitudinally, but such wires may add undesired profile to the device. Even more problematic, when a catheter flexes or torques during standard catheter use, the catheter wall, of necessity, must accommodate the path length differences induced by the different arc lengths of the inside and outside bend radii of the catheter, which leads to both compression and elongation of the wall. During compression, the wire(s) may buckle and subsequently fatigue and/or wear their insulation, while during extension, the wire(s) and any associated insulation may not be able to handle the required elongation without compromising the wire(s) or their insulation. In the case of a wire conductor, the conductor may neck after bending, which may create hot spots, impedance problems, and the like or eventually fatigue and break, e.g., after bending the catheter multiple times as it is manipulated within a patient's body. Changes to electrical properties in any way may be problematic as the conductors are used for many purposes including impedance measurements, high current delivery (e.g., RF ablation), high voltage delivery (e.g., defibrillation), simple tissue voltage/timing measurements, and the like.

Accordingly, there is a need for improved catheters, sheaths, and other tubular devices and methods of their manufacture.

SUMMARY

The present invention is directed to reinforced catheters, sheaths, or other tubular devices including one or more lumens. More particularly, the present invention is directed to catheters, sheaths, or other tubular devices including wires or other conductors braided or otherwise incorporated into the tubular devices, e.g., for electrodes, sensing elements, imaging elements, therapeutic elements, and/or other electrical elements carried by the tubular devices, and to methods for making such tubular devices.

In accordance with one embodiment, a tubular device is provided for a catheter or sheath that includes a proximal end, a distal end sized for introduction into a patient's body, a central lumen extending between the proximal and distal ends, thereby defining a longitudinal axis, an elongate conductor extending at least partially between the proximal and distal ends adjacent the central lumen, one or more reinforcement members comprising windings extending helically around the central lumen between the proximal and distal ends, and an outer jacket surrounding the one or more reinforcement members. In addition, the tubular device may include a first portion in which the conductor extends helically around the central lumen, and a second portion in which the conductor extends substantially parallel to the longitudinal axis and either a) all of the windings surround the central lumen and the conductor remains outside the windings, b) at least some of the windings pass between the central lumen and the conductor and at least some of the windings surround both the central lumen and the conductor, or c) all of the windings surround both the central lumen and the conductor.

In accordance with another embodiment, a tubular device is provided for a catheter or sheath that includes a proximal end, a distal end sized for introduction into a patient's body, a central lumen extending between the proximal and distal ends, thereby defining a longitudinal axis, one or more reinforcement members comprising windings extending helically around the central lumen between the proximal and distal ends, an outer jacket surrounding the one or more reinforcement members, a conductor extending at least partially between the proximal and distal ends adjacent the central lumen, and a steering element extending between the proximal and distal ends within an auxiliary lumen. The tubular device may also include a steerable distal portion adjacent the distal end in which the conductor and steering element extend substantially parallel to the longitudinal axis with the auxiliary lumen offset about ninety degrees around a circumference of the distal portion relative to the conductor, and an intermediate portion proximal to the distal portion in which the conductor extends helically around the central lumen and is braided with the reinforcement members.

In accordance with still another embodiment, a tubular device is provided for a catheter or sheath that includes a proximal end, a distal end sized for introduction into a patient's body, a central lumen extending between the proximal and distal ends, thereby defining a longitudinal axis, one or more reinforcement members comprising windings extending helically around the central lumen between the proximal and distal ends, an outer jacket surrounding the one or more reinforcement members, and a plurality of conductors extending at least partially between the proximal and distal ends adjacent the central lumen. The tubular device may also include a distal portion adjacent the distal end including a plurality of sensing elements spaced apart from one another along the distal portion, each sensing element coupled to at least one of the conductors, and an intermediate portion proximal to the distal portion in which the conductors extend helically around the central lumen and are braided with the reinforcement members.

In accordance with another embodiment, a method is provided for making a tubular body that includes directing a primary mandrel along a central axis of a braiding apparatus such that the primary mandrel is surrounded by a plurality of reinforcement carrying elements in a predetermined configuration relative to the central axis, and providing an elongate conductor dispenser at a first location adjacent to the reinforcement carrying elements and offset from the central axis. With a conductor feeding from the dispenser at the first location, reinforcement members from the reinforcement carrying elements and the conductor from the dispenser are simultaneously wrapping helically around a first portion of the primary mandrel.

The dispenser is moved to a second location, and, with the conductor feeding from the dispenser at the second location, reinforcement members from the reinforcement carrying elements are wrapped helically around a second portion of the primary mandrel while the conductor extends substantially axially along the second portion. Optionally, an outer jacket may be applied around the primary and secondary mandrels after wrapping the one or more reinforcement members therearound, and/or the primary mandrel may be removed to define a primary lumen within the tubular body.

In accordance with yet another embodiment, a method is provided for making a tubular body that includes directing a primary mandrel along a central axis of a braiding apparatus such that the primary mandrel is surrounded by a plurality of reinforcement carrying elements in a predetermined configuration relative to the central axis; providing an elongate conductor dispenser at a first location adjacent to the reinforcement carrying elements and offset from the central axis; with a conductor feeding from the dispenser at the first location, simultaneously wrapping reinforcement members from the reinforcement carrying elements and wrapping the conductor from the dispenser helically around a first portion of the primary mandrel; moving the dispenser to a second location; with the conductor feeding from the dispenser at the second location, wrapping reinforcement members from the reinforcement carrying elements helically around a second portion of the primary mandrel such that the conductor remains outside the reinforcement members; applying an outer jacket around the primary and secondary mandrels after wrapping the one or more reinforcement members therearound; and removing the primary mandrel to define a primary lumen within the tubular body.

In accordance with still another embodiments, a method is provided for making a tubular body that includes directing a primary mandrel along a central axis of a braiding apparatus such that the primary mandrel is surrounded by a plurality of reinforcement carrying elements in a predetermined configuration relative to the central axis; providing an elongate member dispenser at a first location adjacent to the reinforcement carrying elements and offset from the central axis; with an elongate member feeding from the dispenser at the first location, simultaneously wrapping reinforcement members from the reinforcement carrying elements and wrapping the elongate member from the dispenser helically around a first portion of the primary mandrel; moving the dispenser to a second location; with the elongate member feeding from the dispenser at the second location, wrapping reinforcement members from the reinforcement carrying elements helically around a second portion of the primary mandrel while the elongate member extends substantially axially along the second portion; applying an outer jacket around the primary and secondary mandrels after wrapping the one or more reinforcement members therearound; and removing the primary mandrel to define a primary lumen within the tubular body. In exemplary embodiments, the elongate member may include one of a conductor, a fiberoptic bundle, a tensile element, and a stiffening element.

In accordance with another embodiment, a method is provided for making a tubular body using a braiding apparatus comprising a primary mandrel source configured to direct a primary mandrel along a central axis, a plurality of horn gears movably mounted around the central axis in a predetermined arrangement such that the horn gears rotate about respective horn gear axes and carriers travel along a generally circular path around the central axis during operation of the braiding apparatus, and a dispenser configured to direct a conductor towards the primary mandrel from one of a plurality of locations comprising a first location disposed adjacent one of the carriers, a second location aligned with a horn axis of one of the horn gears, a third location outside the generally circular path, and a fourth location adjacent the central axis within the generally circular path.

The method generally includes braiding a first portion of the primary mandrel by: a) directing the primary mandrel along the central axis; b) providing the dispenser at one of the plurality of locations; c) directing the conductor from the dispenser towards the primary mandrel such that the dispenser is disposed adjacent the first portion of the primary mandrel in a first configuration; and d) wrapping reinforcement members from the horn gears around the first portion of the primary mandrel. The method may also include braiding a second portion of the primary mandrel by: a) moving the dispenser to another of the plurality of locations; b) directing the primary mandrel further along the central axis; and c) directing the conductor from the dispenser towards the primary mandrel such that the dispenser is disposed adjacent the first portion of the primary mandrel in a second configuration different than the first configuration; d) wrapping reinforcement members from the horn gears around the second portion of the primary mandrel. Optionally, an outer jacket may be applied around the first and second portions of the primary mandrel and the secondary mandrel, and/or the primary mandrel may be removed to define a primary lumen within the tubular body.

Other aspects and features of the present invention will become apparent from consideration of the following description taken in conjunction with the accompanying drawings.

BRIEF DESCRIPTION OF THE DRAWINGS

The drawings illustrate exemplary embodiments of the invention, in which.

DETAILED DESCRIPTION OF THE EXEMPLARY EMBODIMENTS

Figure 1A:
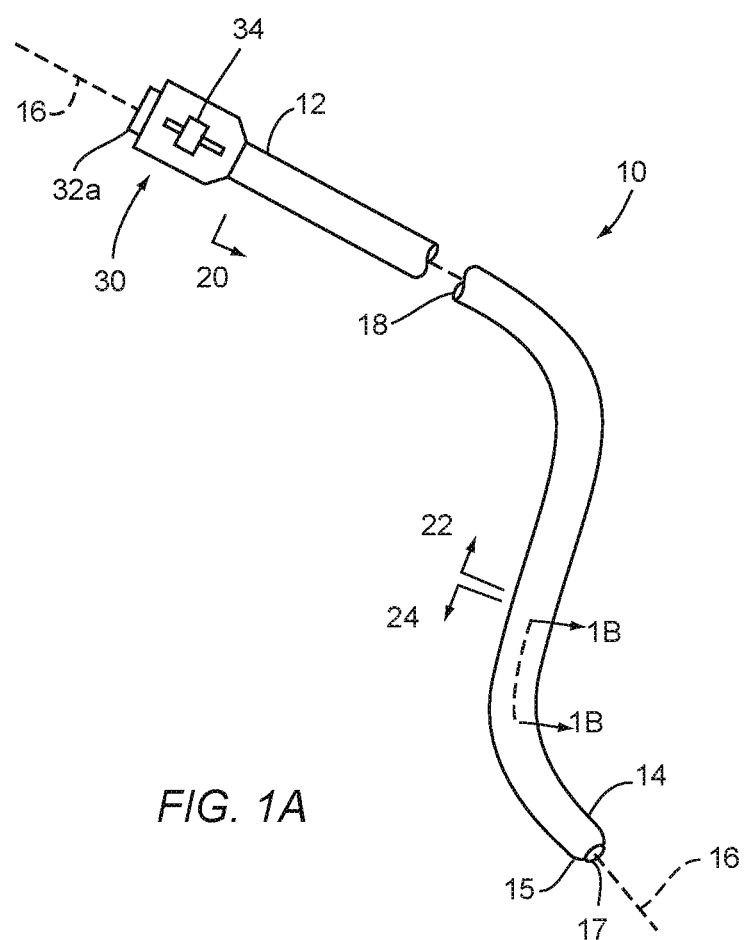
FIG. 1A is a perspective view of an exemplary embodiment of a catheter, including multiple lumens extending between proximal and distal ends thereof, and including a steerable distal portion.
Figure 1B:
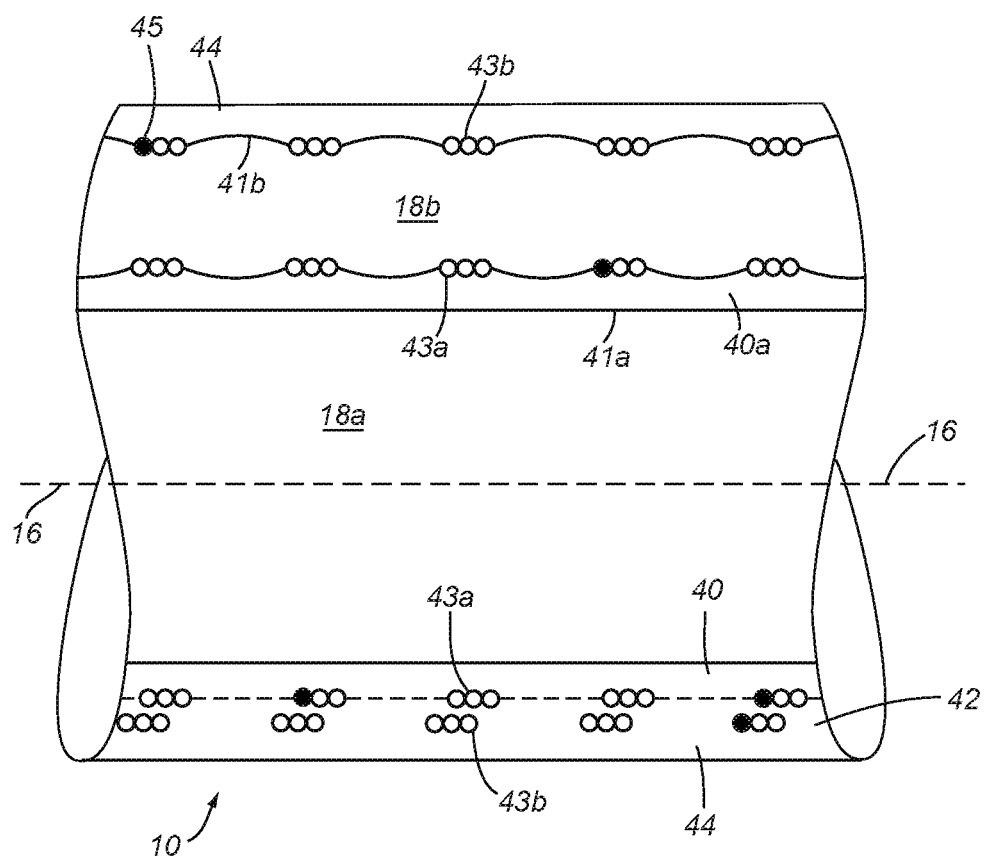
FIG. 1B is a cross-sectional side view of the catheter of FIG. 1A, taken along line 1B-1B, showing reinforcement members positioned around primary and auxiliary lumens of the catheter.

Turning to the drawings, FIGS. 1A and 1B show an exemplary embodiment of an apparatus 10 for introduction into a body lumen (not shown), e.g., for performing a diagnostic and/or therapeutic procedure within a patient's body. In exemplary embodiments, the apparatus 10 may be a guide catheter, a sheath, a procedure catheter, e.g., an imaging catheter, an ablation and/or mapping catheter, a balloon catheter, or other tubular device sized for introduction into a body lumen, such as a vessel within a patient's vasculature, a passage within a patient's gastrointestinal tract, urogenital tract, reproductive tract, respiratory tract, lymphatic system, and the like (not shown). In exemplary embodiments, the apparatus 10 may have a length between about ten and one hundred thirty centimeters (10-130 cm), and an outer diameter between about four and twenty-four French (4-24 Fr or 1.33-8.0 mm).

Generally, the apparatus 10 is an elongate tubular member including a proximal end 12, a distal end 14 sized for insertion into a body lumen or other location within a patient's body, a central longitudinal axis 16 extending between the proximal and distal ends 12, 14, and one or more lumens 18 extending between the proximal and distal ends 12, 14. For example, as shown in FIG. 1B, the apparatus 10 may include a central or primary lumen 18a, e.g., sized for receiving or carrying one or more instruments or other elements (not shown). In exemplary embodiments, the central lumen 18a may be sized for receiving or carrying a guide wire, procedure catheter, balloon catheter, ablation catheter, cardiac lead, needle, or other instrument (not shown), one or more wires or other conductors, one or more optical fibers, one or more tubes or accessory lumens, one or more mechanical elements, one or more sensors, and/or sized for delivering and/or removing fluids or other flowable agents or materials therethrough.

In one embodiment, shown in FIG. 1A, the central lumen 18a may exit at or communicate with an outlet 17 in the distal end 14, e.g., to allow a guidewire or other instrument (not shown) to pass therethrough and/or for delivering or aspirating fluid therethrough. Alternatively, the central lumen 18a may be enclosed, e.g., terminating within or adjacent the distal end, e.g., by an electrode, cap, or other component (not shown) to isolate the central lumen 18a and/or elements carried therein from the environment outside the apparatus 10.

Returning to FIG. 1B, optionally, in addition to the central lumen 18a, the apparatus 10 may include an auxiliary lumen 18b, e.g., extending adjacent the central lumen 18a, e.g., substantially parallel to and radially offset relative to the central axis 16. For example, in an exemplary embodiment, the auxiliary lumen 18b may be a steering element lumen configured to receive a pull wire or other steering element (not shown) therein, e.g., to bend or otherwise deflect a distal portion of the catheter 10, as described further elsewhere herein.

With continued reference to FIGS. 1A and 1B, optionally, the apparatus 10 may include one or more additional lumens (not shown), e.g., one or more additional steering element lumens, conductor lumens, inflation lumens (e.g., if the apparatus 10 includes one or more balloons, not shown on the distal end 14), and/or accessory lumens. For example, a pair of auxiliary lumens may be provided (not shown) on opposite sides of the apparatus 10, e.g., offset about one hundred eight degrees (180°) around the circumference of the apparatus 10 from one another, e.g., for receiving respective steering elements.

Optionally, the auxiliary lumen(s) may have a variety of cross-sectional shapes and/or sizes, e.g., a substantially circular shape, an elliptical or oval shape, a substantially rectangular shape, a triangular shape, a pair of overlapping circles shape, and the like, e.g., similar to the devices disclosed in U.S. Publication No. 2014/0323964, the entire disclosure of which is expressly incorporated by reference herein. The shape and/or size of the auxiliary lumen(s) may be substantially uniform along the length of the apparatus 10 or may vary at different locations, as described elsewhere herein.

The auxiliary lumen 18b is generally radially offset from the central axis 16 substantially along the length of the apparatus 10, e.g., entirely from the distal end 14 to the proximal end 12. In addition, the radial and/or circumferential position of the auxiliary lumen 18*b* may change relative to the primary lumen 18*a* and/or other components of the apparatus 10 at various locations along the length of the apparatus 10, as described elsewhere herein and in the references incorporated by reference herein.

Returning to FIG. 1A, the distal end 14 may include a tapered, rounded, or otherwise shaped distal tip 15, e.g., to provide a substantially atraumatic tip and/or to facilitate advancement or navigation through various anatomy. In addition or alternatively, the distal end 14 may include one or more therapeutic and/or diagnostic elements, e.g., one or more balloons, stents, sensors, electrodes, ablation elements, thermocouples, steering mechanisms, imaging devices, helical anchors, needles, and the like (not shown), depending upon the particular intended application for the apparatus 10. Further, in addition or alternatively, the distal end 14 may include one or more markers or other features to enhance radiopacity and/or visibility under ultrasound, MRI or other imaging modalities, e.g., by mounting one or more platinum elements on the distal end 14, doping one or more regions of the distal end 14 with tungsten or barium sulfate, and/or other methods known in the art.

Optionally, as shown in FIG. 1A, the proximal end 12 may include a handle or hub 30, e.g., configured and/or sized for holding and/or manipulating the apparatus 10 from the proximal end 12. In addition, the handle 30 may include one or more ports, e.g., port 32*a* communicating with the central lumen 18*a*, or other respective lumens (not shown). Optionally, the port 32*a* may include one or more valves, e.g., a hemostatic valve (also not shown), which may provide a substantially fluid-tight seal, while accommodating insertion of one or more instruments or fluids into the central lumen 18*a*. Optionally, a side port (not shown) may be provided on the handle 30, e.g., for delivering fluid into and/or aspirating fluid from the primary lumen 18*a*, e.g., around an instrument inserted into the primary lumen 18*a*. Optionally, the handle 30 and/or proximal end 12 may include one or more connectors, such as luer lock connectors, electrical connectors, and the like, for connecting other devices (not shown) to the apparatus 10, such as syringes, displays, controllers, and the like (also not shown).

In addition, the handle 30 may include one or more actuators, such as sliders, buttons, switches, rotational actuators, and the like, e.g., for activating and/or manipulating components (also not shown) on the distal end 14 or otherwise operating the apparatus 10. For example, as shown in FIG. 1A, an actuator 34 may be provided that is coupled to a proximal end of a steering element (not shown) within the auxiliary lumen 18*b*, e.g., as described further elsewhere herein.

Generally, with particular reference to FIG. 1B, the apparatus 10 may include an inner liner 40, e.g., at least partially or entirely surrounding or otherwise defining the central lumen 18*a*, a reinforcement layer 42 surrounding the inner liner 40, and an outer jacket 44 surrounding and/or encasing the reinforcement layer 42, each of which may extend at least partially between the proximal and distal ends 12, 14 of the apparatus 10. The reinforcement layer 42 and/or outer jacket 44 may be attached to the inner liner 40, e.g., by laminating, adhering, adhesive bonding, ultrasonic welding, reflowing or other heating, and the like, as described elsewhere herein.

In an exemplary embodiment, the central lumen 18*a* is defined by an inner liner 40*a* including an inner surface 41*a*. The inner liner 40*a* may be formed from lubricious material, e.g., PTFE, to provide a lubricious inner surface 41*a*. Alternatively, the inner liner 40 may be formed from one or more layers of thermoplastic or other polymeric material including one or more coatings on the inner surface 41*a* having desired properties, e.g., a hydrophilic and/or lubricious coating, e.g., similar to the liners disclosed in U.S. Pat. Nos. 7,550,053 and 7,553,387, and U.S. Publication No. 2009/0126862, the disclosures of which are expressly incorporated by reference herein.

Optionally, as shown in FIG. 1B, an inner liner 40*b* may also at least partially surround the auxiliary lumen 18*b*, which may be formed from a lubricious material and/or may include one or more coatings on its inner surface 41*b*, similar to the inner liner 40*a*. The inner surface 41*b* of the auxiliary lumen 18*b* may have a substantially uniform cross-section, as shown in FIG. 1B. Alternatively, the inner surface 41*b* of the auxiliary lumen 18*b* may have a textured or other variable cross-section along, e.g., along its length and/or about its circumference (not shown).

Optionally, any or all of the inner liner 40*a*, reinforcement layer 42, and/or outer jacket 44 may be formed from multiple layers of like or different materials (not shown), e.g., to provide desired material properties in the different portions of the apparatus 10. In an exemplary embodiment, the outer jacket 44 may be formed from PEBAX, nylon, urethane, and/or other thermoplastic material, e.g., such that the material of the outer jacket 44 may be heated and reflowed and/or otherwise formed around the components defining the lumens 18, e.g., as described elsewhere herein.

In one embodiment, one or more of the layers of the apparatus 10 may have a substantially homogenous construction between the proximal and distal ends 12, 14. Alternatively, the construction may vary along the length of the apparatus 10 to provide desired properties, e.g., between proximal, intermediate, and distal portions 20, 22, 24. For example, a proximal portion 20 of the apparatus 10 adjacent the proximal end 12 may be substantially rigid or semi-rigid, e.g., providing sufficient column strength to allow the distal end 14 of the apparatus 10 to be pushed or otherwise manipulated from the proximal end 12, while the distal portion 24 may be substantially flexible. As described further below, the distal portion 24 of the apparatus 10 may be steerable, i.e., may be bent, curved, or otherwise deflected in a desired manner, e.g., substantially within a steering plane, as described further below.

Figure 4A:
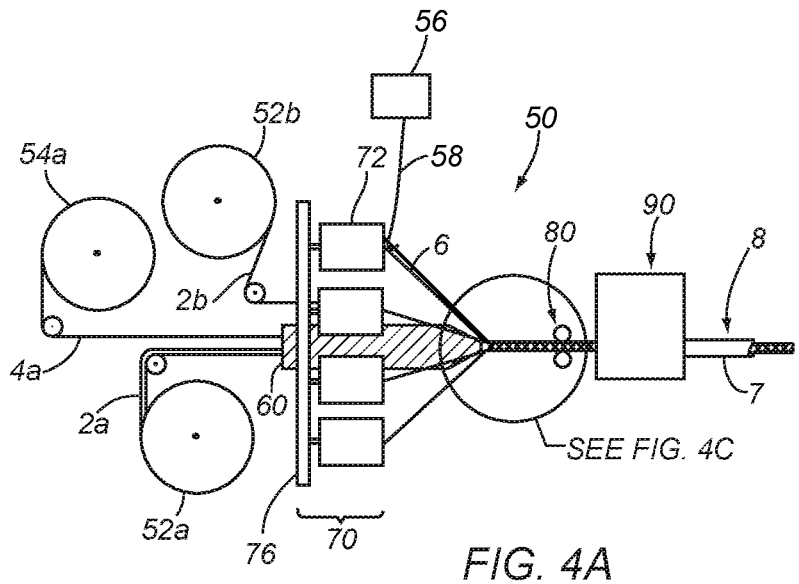
FIG. 4A is a schematic of an exemplary embodiment of a braiding apparatus for making a reinforced tubular member including multiple mandrels supported by reinforcement members.
Figure 4B:
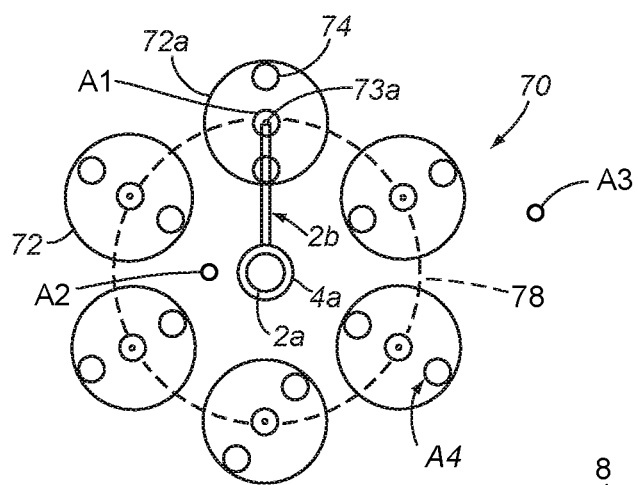
FIG. 4B is a front view of an arrangement of horn gears for creating a braided configuration of reinforcement members that may be included in the braiding apparatus of FIG. 4A and including various locations for dispensers carrying conductors.

Returning to FIG. 1B, the reinforcement layer 42 may include one or more reinforcement members 43, e.g., wound in a braided or other helical configuration around the inner liner 40*a*, e.g., using a braiding apparatus such as that shown in FIGS. 4A and 4B, and the outer jacket 44 may include one or more tubular layers surrounding the reinforcement layer 42 and/or between the reinforcement layer 42 and the inner liner 40*a*. In an exemplary embodiment, the reinforcement layer 42 may include one or more, or a plurality of, round or flat (e.g., rectangular, elliptical, or flat oval) wires, filaments, strands, or other reinforcement members 43, e.g., formed from metal, such as stainless steel, plastic, such as PEEK, glass, woven or twisted fibers, such as aramid, and the like, or composite materials.

In one embodiment, a plurality of reinforcement members 43 may be braided around the inner liner 40*a*, e.g., with each reinforcement member 43 having the same material and/or shape. Alternatively, the reinforcement members 43 may have different sizes and/or shapes, e.g., a first size or shape extending helically in a first direction and a second size or shape (different than the first) extending helically in a second direction (e.g., opposite the first direction).

The reinforcement layer 42 may be configured to substantially transfer torsional forces between the proximal and distal ends 12, 14, e.g., to allow the apparatus 10 to be twisted from the proximal end 12 to rotate the distal end 14 about the longitudinal axis 16 within a patient's body. In addition, the reinforcement layer 42 may allow the distal end 14 of the apparatus 10 to be advanced or otherwise manipulated within a patient's body from the proximal end 12 without substantial risk of buckling and/or kinking. The pitch of the reinforcement layer 42 may be varied along the length of the apparatus 10, e.g., in order to optimize mechanical properties of various segments or portions of the apparatus 10.

Figure 2A:
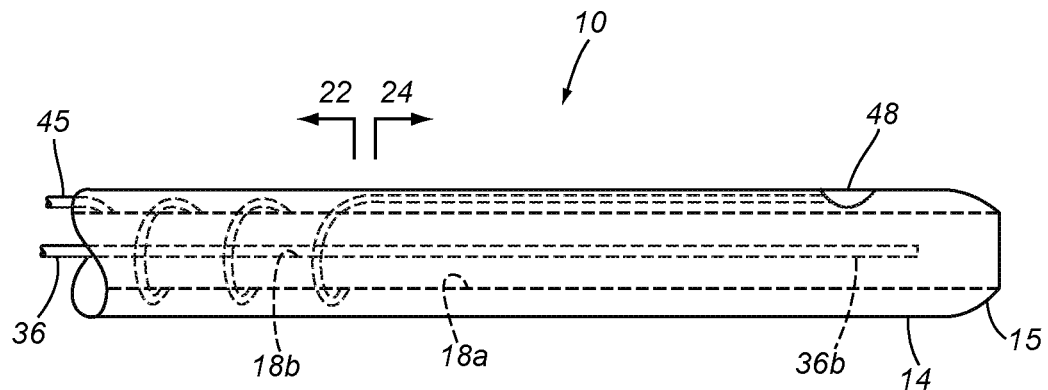
FIGS. 2A and 2B are top and side views, respectively, of an exemplary embodiment of a catheter including an elongate wire helically braided along an intermediate portion of the catheter and extending substantially axially along a distal portion of the catheter.
Figure 2B:
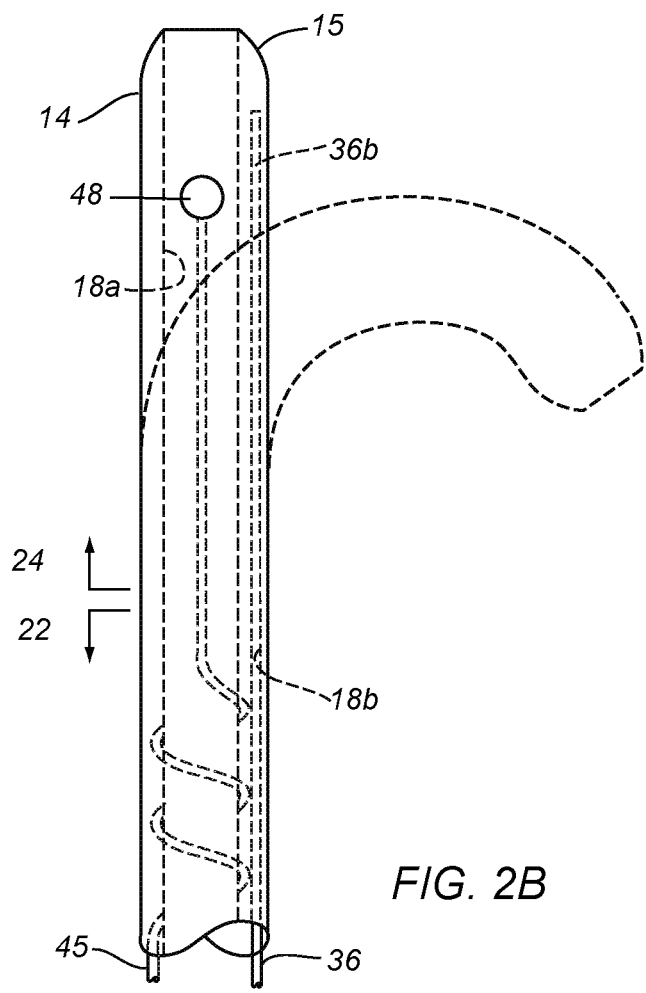

In addition, as shown in FIGS. 2A and 2B, the apparatus 10 may include one or more elongate wires or conductors 45 extending at least partially between the proximal and distal ends 12, 14. The conductor(s) 45 may be coupled to one or more electrodes, sensors, imaging devices, actuators, therapeutic elements, and/or other electrical components on the apparatus 10, e.g., a plurality of electrodes or sensors spaced apart from one another on the distal portion 24 of the apparatus 10 (one exemplary electrode 48 shown in FIGS. 2A and 2B).

In exemplary embodiments, the conductor(s) 45 may include a metal or other conductive core encased in insulation, e.g., to electrically isolate the conductor(s) 45 from the reinforcement members 43 and/or other components of the apparatus 10. Exemplary materials for the conductor(s) 45 and/or electrodes 48 may include platinum and/or platinum alloys (e.g., including iridium, and the like), gold, and/or other precious metals and/or highly conductive metals and/or other conductive materials (e.g., carbon elements, stainless steel). Further alternatives may include wire having a silver core and cobalt chromium alloy jacket, e.g., a highly conductive core with an outer layer for mechanical strength. Conductors may include an electrical insulation layer and/or coating, which in certain cases may also improve mechanical properties, e.g., PTFE, FEP, polyimide, silicone, parylenes, etc. Plating of gold, platinum, and/or other desirable materials may also be used for the electrodes 48.

The location of the conductor(s) 45 may vary relative to the central lumen 18a and/or the reinforcement layer 42 (not shown in FIGS. 2A and 2B, see, e.g., FIG. 1B) along different portions of the apparatus 10. For example, along a first portion, e.g., the intermediate portion 22 shown in FIGS. 2A and 2B, the conductor(s) 45 may extend helically around the central lumen 18a, e.g., braided along with the reinforcement members 43, as shown in FIG. 1B. Along a second portion, e.g., the distal portion 24 shown in FIGS. 2A and 2B, the conductor(s) 45 may extend substantially longitudinally or axially relative to the central lumen 18a, which may facilitate coupling the conductor(s) 45 to one or more electrodes or sensors, e.g., electrode 48.

In addition or alternatively, the location of the conductor(s) 45 may vary relative to the outer jacket 44 and/or reinforcement layer 42. For example, the conductor(s) 45 may be braided along with the reinforcement members 43 along a first portion, e.g., the intermediate portion 22, while along a second portion, e.g., the distal portion 24, the conductor(s) 45 may be disposed outside the reinforcement layer 42, e.g., which may facilitate accessing the conductor(s) 45 through the outer jacket 44 during fabrication, as described elsewhere herein. Alternatively, the conductor(s) 45 may be captured within the reinforcement layer 42 or surrounded by the reinforcement layer 42 while extending longitudinally, as described further elsewhere herein.

Optionally, as shown in FIGS. 2A and 2B, the distal portion 24 of the apparatus 10 may be steerable or deflectable, e.g., using one or more pull wires, cables, fibers, threads, filaments, or other steering elements, such as a pull wire 36 slidably received within auxiliary lumen 18b. The steering element 36 generally includes a proximal end (not shown) coupled to an actuator, e.g., such as the actuator 34 on the handle 30 shown in FIG. 1A, and extends from a proximal portion (not shown) through the intermediate portion 22 and into the distal portion 24. A distal end 36b of the steering element 36 may be fixed or otherwise coupled to the distal end 14, e.g., to a ring or other component (not shown) defining or adjacent the distal tip 15.

The steering element 36 may be formed from materials capable of substantially transferring any axial forces applied at the proximal end 12 to the distal end 14, as is known in the art. Optionally, the steering element 36 may include a coating, e.g., PTFE, parylene, silicone, or other lubricious material, an outer sleeve, e.g., formed from HDPE, PTFE, and the like, to reduce friction between the steering element and the wall of the auxiliary lumen 18b. Alternatively or in addition, the inner surface of the auxiliary lumen 18b may be formed from lubricious material and/or may include one or more coatings, as described elsewhere herein. Alternatively or in addition, the auxiliary lumen 18b may include one or more incompressible elements, e.g., a tightly wound coil therearound, e.g., to prevent compression, which may otherwise lead to creating a bending moment along at least part of its length.

During use, the actuator may be activated, e.g., directed proximally or distally relative to the handle and/or the proximal end (not shown), to apply an axial force to the steering element 36, e.g., tension (when the steering element is pulled) or compression (when the steering element is advanced). Because the steering element 36 is slidable within the auxiliary lumen 18b, the axial force is translated and applied to the distal end 36b coupled to the distal end 14. Further, because the auxiliary lumen 18b is offset from the central axis 16 along at least the distal portion 24, the axial force applies a bending moment, thereby causing the distal portion 24 to curve, bend, or otherwise deflect in a desired plane or other manner (e.g., as shown in phantom in FIG. 2B). Optionally, the proximal and intermediate portions 20, 22 of the apparatus 10 may be constructed to prevent or minimize bending forces caused by actuation of the steering element 36.

Optionally, in the configuration shown in FIGS. 2A and 2B, along the distal portion 24, a distal segment of the auxiliary lumen 18b may be surrounded by the reinforcement layer 42 (not shown), e.g., immediately adjacent the central lumen 18a, and then may transition such that an intermediate segment of the auxiliary lumen 18b is outside the reinforcement layer 42, e.g., closer to an outer surface of the apparatus 10 along at least the intermediate portion 22 (and/or optionally along the proximal portion 20 to the proximal end 12 and/or handle 30, not shown; see FIG. 1A). Alternatively, the intermediate segment may be braided into the reinforcement layer 42.

One potential advantage of the apparatus 10 is that the conductor 45 may be offset around the circumference of the distal portion 24 relative to the auxiliary lumen 18b, e.g., about ninety degrees (90°). Thus, the conductor 45 may be offset about ninety degrees outside the plane of curvature or deflection (e.g., within the plane of FIG. 2B) such that compression and/or extension of the conductor 45 is minimized. In contrast, if the conductor 45 were positioned axially adjacent the auxiliary lumen 18b, the conductor 45 would be compressed when the distal portion 24 was deflected towards the side including the conductor 45 and extended when the distal portion 24 was deflected in the opposite direction within the plane. Such compression and/or extension of the conductor 45 may risk damage to the conductor 45, as explained elsewhere herein. Another potential advantage is that the conductor 45 may be positioned outside the plane of deflection and therefore may not resist bending of the distal portion 24 within the plane.

Figure 3A:
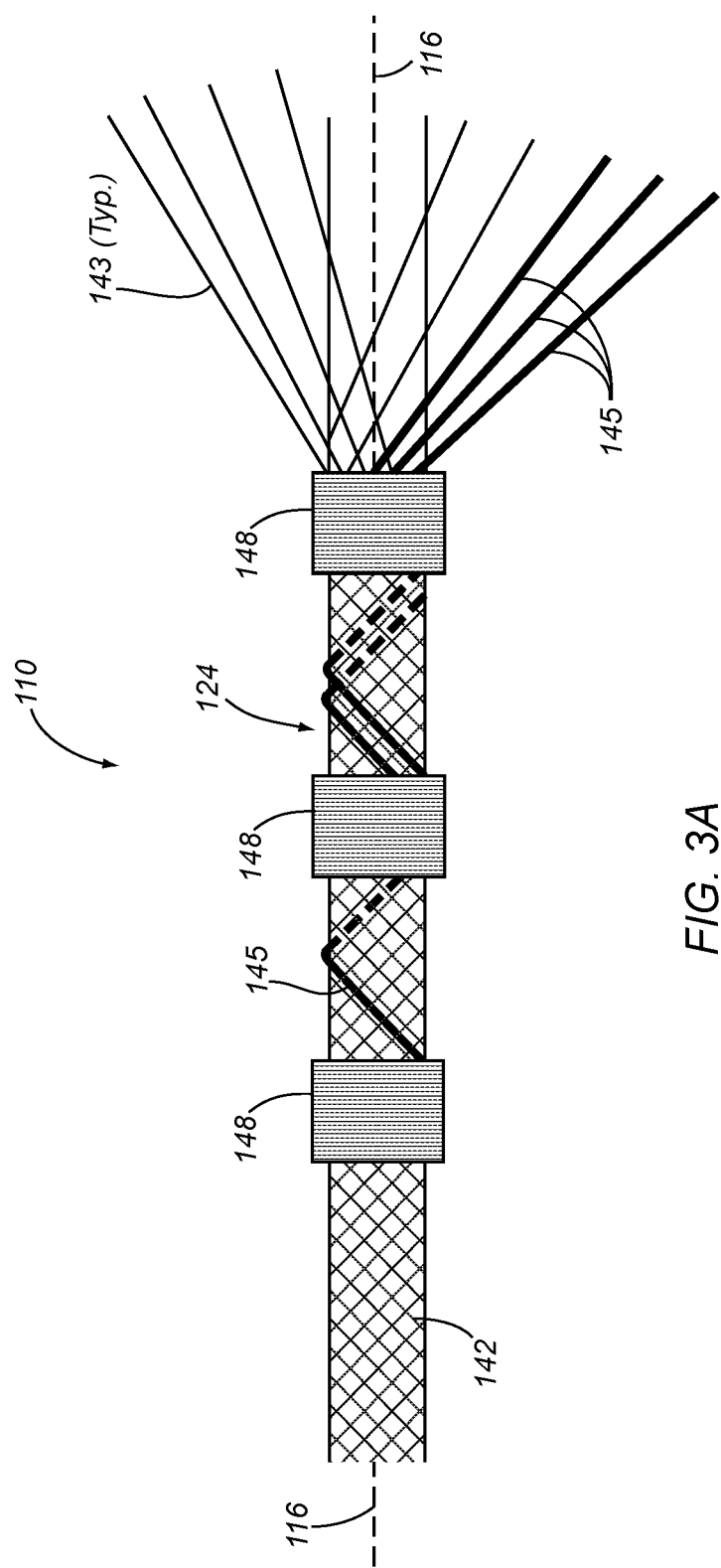
FIG. 3A is a detail of a distal portion of an exemplary embodiment of an assembly for a tubular device including a plurality of electrodes and wires incorporated into a reinforcing layer of the assembly.
Figure 3B:
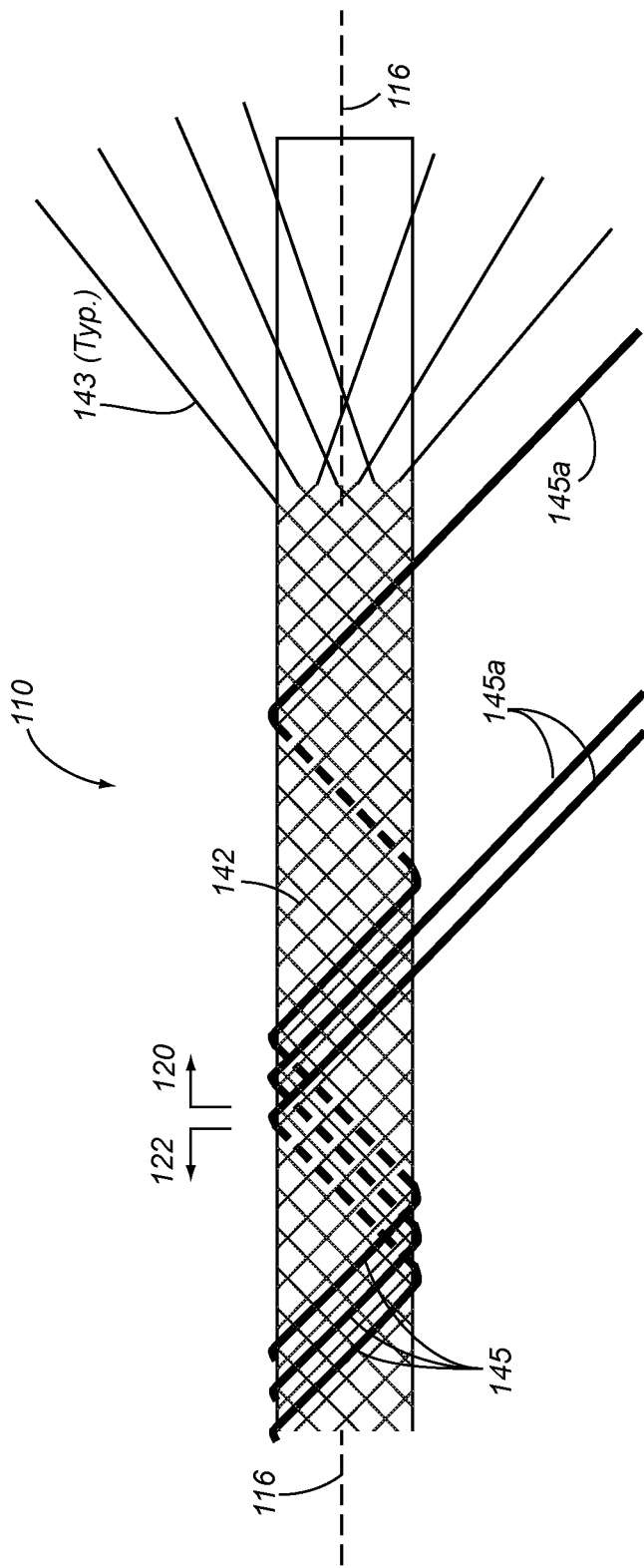
FIG. 3B is a detail of a proximal portion of an exemplary embodiment of an assembly for a tubular device including a plurality of wires incorporated into a reinforcing layer of the assembly and exiting the assembly.

Turning to FIGS. 3A and 3B, in another embodiment, an apparatus 110 may be provided that includes a plurality of sensors, actuators, electrodes, imaging elements, and/or or other components 148 on a distal portion 124 of the apparatus 110, which may be coupled to one or more wires or conductors 145 extending helically and proximally from the distal portion 124 (shown in FIG. 3A), e.g., through an intermediate portion 122 to a proximal portion 120 (shown in FIG. 3B), and the conductors 145 may be coupled to one or more connectors and/or electronics at the proximal end (not shown) of the final apparatus 110.

In the exemplary embodiment shown, the conductors 145 may be braided into the reinforcement layer 142, e.g., at least along the intermediate portion 122, such that the conductors 145 extend helically in the same direction adjacent one another. Optionally, the conductors 145 may be disposed immediately adjacent one another, e.g., such that there are no reinforcement members 143 between the conductors 145. Alternatively, the conductors 145 may be positioned immediately adjacent to a reinforcement member 143, e.g., as shown in FIG. 3B, which may enhance protection of the conductors 145. For example, during the braiding process, any contact by other reinforcement members 143 being braided around the apparatus 110 may be directed to the adjacent reinforcement members 143, which may protect the insulation and/or minimize abrasion or undesired contact with the conductors 145, e.g., if at least one adjacent reinforcement member 143 is larger in diameter or other cross-section than the conductor 145.

Optionally, the conductors 145 may transition to positions outside the reinforcement layer 142, e.g., at one or more axial locations on the proximal portion 120, e.g., for a relatively short distance. This position may facilitate accessing free ends 145a of the conductors 145, e.g., to couple the conductors 145 to components within a handle (not shown) of the final apparatus 110 and/or to form and/or modify the exposed conductor, e.g., to form an electrode. Alternatively, the conductors 145 may simply exit an outer jacket (not shown) of the final apparatus 110 at one or more locations along the proximal portion 120. For example, as shown, the conductors 145 may exit at locations spaced apart from one another. Alternatively, the conductors 145 may exit at the same axial location, e.g., at different positions around the circumference of the proximal portion 120 (not shown).

Figure 4C:
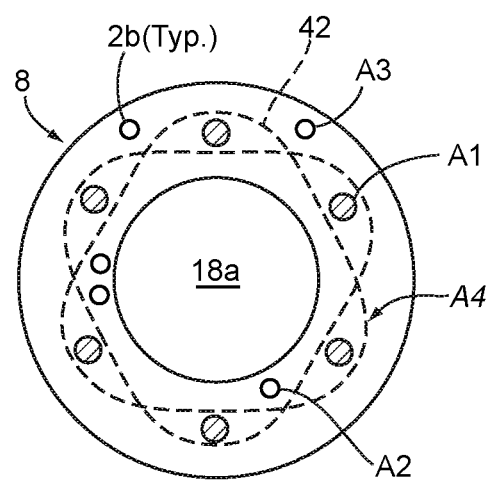
FIG. 4C is a cross-sectional view of a catheter showing the locations of a conductor corresponding to different locations for the conductor dispensers shown in FIG. 4B.

Turning to FIGS. 4A-4C, various methods may be used for manufacturing and/or assembling any of the embodiments described herein. For example, FIG. 4A shows an exemplary embodiment of an apparatus 50 for making one or more tubular bodies, such as catheters and/or components for catheters, sheaths, or other tubular devices 8. Generally, the apparatus 50 includes one or more plurality of sources 52, 54 of mandrels 2 and/or liners 4, a guide 60, one or more dispensers or other sources of conductors 56, a source 70 of reinforcement members 6, a drive mechanism 80, and, optionally, a source 90 of jacket material 7.

While mandrels, liners, and/or jackets may be provided in discrete segments (not shown), the apparatus 50 may allow for substantially continuous fabrication of tubular bodies, e.g., wrapping a liner material 4a around a primary mandrel 2a (or the primary mandrel 2a may include a tubular or other liner material provided around it on the source 52, e.g., similar to the liners disclosed in the references incorporated by reference elsewhere herein), positioning an auxiliary mandrel 2b (with optional liner material, not shown) adjacent the primary mandrel 2a, braiding a plurality of reinforcement members 4 around the mandrels 2, adding one or more conductors 58, and optionally, applying outer jacket material 7 around the reinforced mandrels, as described further below.

As used herein, "substantially continuous" means that the apparatus 50 and/or method may operate indefinitely, i.e., to make as few as one or as many as hundreds or thousands of tubular bodies 8, e.g., by substantially simultaneously feeding components of the tubular bodies 8 from sources 52, such as reels, through components of the apparatus 50 until the sources 52 are depleted, whereupon new source(s) may be loaded onto the apparatus 50 and the process continued. Alternatively, the apparatus 50 may be used to create discrete lengths of tubular devices, e.g., if the mandrels and/or liners are provided in specific lengths corresponding to one or more individual tubular devices (not shown). In a further alternative, some of the operations may be performed substantially continuously, while other operations are performed on components intended for one or more individual tubular devices.

Thus, the apparatus 50 and methods herein may be used to make one or more relatively long tubular bodies 8, e.g., that are substantially longer than finished catheters or other tubular devices. For example, one resulting tubular body 8 may be collected, e.g., on a take-up reel or container (not shown), or may be separated into individual shorter tubular bodies, e.g., using a cutter or other tool (not shown), that may be incorporated into individual catheters or other tubular devices, e.g., as described elsewhere herein and/or as disclosed in U.S. Publication No. 2009/0126862, the entire disclosure of which is expressly incorporated by reference herein.

With particular reference to FIG. 4A, the apparatus 50 may include one or more sources 52 of mandrels 2, which may be fed into a guide 60 to define lumens of the tubular bodies 8. For example, a first reel 52a may include an elongate primary mandrel 2a, e.g., shaped and/or configured to define a primary or central lumen (not shown) of the tubular bodies 8. Similarly, a second reel 52b may include an elongate auxiliary mandrel 2b, e.g., shaped and/or configured to define a secondary or auxiliary lumen (also not shown) of the tubular bodies 8. As described further below, the second reel 52b or other source of auxiliary mandrel may be located at one of a plurality of available locations during operation to configure the tubular bodies 8 in a desired manner. Optionally, if additional lumens are desired for the tubular bodies 8, one or more additional auxiliary mandrels may be provided (not shown), which may also be moved to one or more locations.

The mandrels 2 may have desired cross-sectional shapes and/or sizes corresponding to the desired cross-sections of the lumens, e.g., substantially circular or other shapes, as described elsewhere herein. The mandrels 2 may be a solid or hollow wire or other cylindrical member having a diameter (or other cross-section) corresponding to the diameter of the lumen to be lined by the strip 24, e.g., between about 0.005-0.300 inch (0.125-7.5 mm), 0.014-0.092 inch (0.35-2.3 mm), or 0.014-0.045 inch (0.35-1.15 mm). In an exemplary embodiment, the auxiliary mandrel 2b may have a substantially smaller diameter or other cross-section than the primary mandrel 2a. In exemplary embodiments, the mandrels 2 may be formed from beading or monofilament material, for example, lubricious material, e.g., PTFE or other fluoropolymer, silicone-treated Acetal, PTFE-coated stainless steel, Parylene-coated stainless steel, silver coated copper, and the like, having sufficient flexibility to allow the mandrels 2 to be wound onto a source reel 52 and/or onto a take-up reel (not shown) after being incorporated into a tubular body 8.

Alternatively or in addition, the mandrels 2 may have a tubular liner predisposed about them, e.g., a fluoropolymer sleeve or coating or other tubular material which may facilitate removal of the mandrel 2 and/or be left behind upon removal of the mandrel 2 to form a liner. Further alternatively, a shim (not shown) may be positioned over a mandrel 2 and/or within a tubular or strip liner such that the shim (not shown) may facilitate creation of a lumen that is larger than the mandrel 2 with or without ultimate removal of the mandrel 2. For example, a PTFE tube or strip shim (not shown) may be positioned around a mandrel 2 and inside of a strip or tubular liner. The mandrel/shim/liner assembly may then be incorporated into a braided shaft or finished apparatus. The shim (not shown) may be subsequently removed, e.g., after braiding, lamination, etc., to leave a lumen larger than the mandrel. After this, the mandrel may remain in place, for example, in the case of the auxiliary mandrel 2b to serve as a pull wire, or simply removed with less force.

In an alternative embodiment, the mandrels 2 may be formed from material that substantially maintains its size and/or shape during fabrication of the tubular bodies, yet may be reduced in cross-section after fabrication to facilitate removal. For example, silver-coated copper wire, PTFE beading, or other malleable metals or polymers may be used for the mandrels 2 that, after fabrication of the tubular body 8, may be necked down before and/or during removal. For example, after fabricating a tubular body 8, the mandrels 2 (or the entire tubular body) may be pulled at one or both ends, thereby causing the mandrels 2 to plastically elongate and thereby reduce their outer cross-section slightly, which may reduce friction between the mandrels 2 and the surrounding liners, reinforcement members, and/or other materials, and thereby facilitate removal. Further alternatively, the mandrels 2 may include a rolled strip with inherent radial strength capable of supporting a lumen during braiding and/or lamination and/or other processing, but may subsequently be constrained, stretched, or otherwise removed. Further alternatively, the mandrels 2 may be constructed from material having relatively high thermal expansion such that during heating, lamination, and/or reflow, the mandrels 2 expand and upon cooling contract, thereby creating a lumen larger than the original mandrel 2.

In yet another alternative, the mandrels 2 may be formed from materials that may be dissolved, e.g., after fabrication, leaving the surrounding materials intact to define the lumens.

In still another alternative, tubular mandrels may be used that have sufficient hoop strength to resist deformation under the forces encountered during braiding and/or other fabrication and/or heating or other processing parameters experienced during fabrication. In this alternative, the tubular mandrels may remain substantially within the tubular bodies 8 after fabrication, e.g., to define the auxiliary lumen. For example, a relatively thick walled PTFE, a lined or bare polyimide tube, or other tubular mandrel may be used. Alternatively, the inner diameter of such a tubular mandrel may be temporarily supported by a temporary supporting mandrel (not shown), e.g. during braiding, and the temporary supporting mandrel may be removed prior to subsequent fabrication and/or heating or other processing steps, e.g., if the tubular mandrel is to remain as a permanent component of the tubular bodies.

Optionally, a source 54 of liner material 4 may be provided for one or both mandrels 2. For example, as shown, a source 54a of liner material 4a is provided such that the liner material 4a may be wrapped at least partially around the primary mandrel 2a, e.g., as the primary mandrel 2a and liner material 4a are fed through the guide 60. The liner material 2a may be formed from lubricious material and/or may include one or more coatings (not shown) on an inner surface thereof oriented towards the primary mandrel 2a, which may provide an inner liner for a primary lumen of the resulting tubular bodies 8a.

For example, the liner material may include a base material, e.g., a relatively thin-walled polymer sheet having a width corresponding to the circumference of the corresponding mandrel, e.g., thermoplastics, such as polyether block amide, urethane, nylon, and the like, fluoropolymers, such as PTFE, FEP, TFE, and the like, thermoset, and thermoform plastics, such as polyimide or polyester, and the like. In exemplary embodiments, the liner material may have a thickness between about 0.0001-0.050 inch (0.0025-1.25 mm), 0.0001-0.003 inch (0.0025-0.076 mm), 0.0001-0.0015 inch (0.0025-0.038 mm), or 0.0005-0.002 inch (0.0125-0.05 mm).

Optionally, if desired a source of liner material may also be provided for the auxiliary mandrel 2b and/or for other auxiliary mandrels (not shown for simplicity). In this option, a guide (also not shown) may be provided for wrapping the liner material around the auxiliary mandrel 2b, e.g., before the auxiliary mandrel 2b is positioned adjacent the primary mandrel 2a. In an alternative embodiment, tubular liner material may be provided on one or both mandrels when loaded on the source 52, and/or may be fed onto the desired mandrel in discrete segments (not shown) before passing the mandrels 2 through the guide 60 or horn gear 72.

With additional reference to FIGS. 4A and 4B, the source 70 of reinforcement members 6 may provide one or more, e.g., a plurality of, reinforcement members 6 that may be wrapped around the mandrels 2, e.g., upon exiting the guide 60. In the exemplary embodiment shown in FIG. 4B, the reinforcement source 70 may include an arrangement of horn gears 72, e.g., mounted in a generally circular configuration around the guide 60, for example, to a base or other support structure 76. The horn gears 72 may be free to rotate about their individual central axes but may be substantially fixed translationally relative to one another and the guide 60. Alternatively, the horn gears 72 may be rotatable relative to the guide 60, e.g., around a central axis of the guide 60, e.g., along a path 78 shown in FIG. 4B, while maintaining their same circular configuration, e.g., by rotating the base 76 relative to the guide 60, as described further elsewhere herein.

The dispenser(s) 56 may be provided at one or more locations, e.g., to locate the conductor(s) 58 at one or more positions and/or configurations relative to the primary mandrel 2a and/or the reinforcement members 6. For example, during fabrication, a dispenser 56 may be moved to one or more locations to change the position and/or configuration of the conductor 58, e.g., to fabricate any of the tubular devices described elsewhere herein. For example, as shown in FIG. 4B, during operation of the apparatus 50, the dispenser 56 may be positioned at locations A1, A2, A3, and/or A4, e.g., for a predetermined time and/or distance along the primary mandrel 2a, and, as desired, moved to one of the other locations one or more times. Thus, in this manner, the location of the conductor 58 may be adjusted, e.g., as shown in FIG. 4C and as described elsewhere herein.

Similarly, the auxiliary mandrel 2b may be moved to different locations relative to the horn gears 72, e.g., to position the auxiliary mandrel 2b relative to the primary mandrel 2a and/or reinforcement members 6. For example, as shown in FIG. 4B, during operation of the apparatus 50, the source of auxiliary mandrel 2b may be positioned at locations A1, A2, A3, or A4, e.g., for a predetermined time and/or distance along the primary mandrel 2a, and, as desired, moved to one of the other locations one or more times. Thus, in this manner, the location of the auxiliary mandrel 2b may be adjusted, which may result in the location of an auxiliary lumen defined by the auxiliary mandrel 2b being moved to desired locations, as shown in FIG. 4C and as described elsewhere herein and in the references incorporated by reference herein.

For example, in the A4 location shown in FIGS. 4A-4C, the dispenser 56 may be positioned adjacent a carrier 74 of one of the horn gears 72, e.g., such that the conductor 58 is directed towards the primary mandrel 2a along with or in place of a reinforcement member 6. Thus, at this location, as the carrier 74 travels along the generally circular path 78 of the horn gears 72, the reinforcement member 6 and conductor 58 may both be braided around the primary mandrel 2a along with the other reinforcement members 6. From this location, the conductor 58 may be wrapped helically around the primary mandrel 2a immediately adjacent the reinforcement member 6, as described elsewhere herein. Alternatively, the dispenser 56 may be carried on the horn gears 72 similar to one of the carriers 74, e.g., such that the conductor 58 is wrapped helically around the primary mandrel 2a independently of the other reinforcement members 6, i.e., is braided around the primary mandrel 2a, optionally in place of one of the reinforcement members 6. It will be appreciated that a plurality of dispensers and conductors (not shown) may be positioned at the same A4 position or at other A4 positions (i.e., adjacent to or in place of one or more carriers) such that multiple conductors 58 are wrapped helically around the primary mandrel 2a, e.g., immediately adjacent one another or spaced apart from one another in a desired configuration (e.g., in the same helical direction with one or more reinforcement members between adjacent conductors, not shown).

If desired, the dispenser(s) 56 may be moved to location A1, i.e., such that conductor 58 is delivered along a central axis of one of the horn gears 72a. For example, the horn gear 72a may include a passage 73a therethrough, e.g., aligned with the central axis of the horn gear 72a, and the conductor 58 may pass through the passage 73a, e.g., from the dispenser 56 towards the primary mandrel 2a where it exits the guide 60. Optionally, if additional conductors are to be provided in the tubular bodies 8, one or more additional horn gears may also include such passage(s) and/or guide(s) for guiding corresponding conductor(s) therethrough.

In the A1 location, the conductor 58 may extend substantially axially along the primary mandrel 2a, yet may be at least partially braided into the reinforcement members 6 adjacent the primary mandrel 2a, i.e., with some reinforcement members 6 surrounding both the primary mandrel 2a and the auxiliary mandrel 2b, and some reinforcement members 6 surrounding only the primary mandrel 2a, as identified by conductor A1 shown in FIG. 4C. By comparison, in location A2, i.e., with the conductor 58 directed immediately adjacent the primary mandrel 2a, e.g., through the guide 60, all of the reinforcement members 6 may surround both the primary mandrel 2a and the conductor 58, thereby positioning the conductor 58 closest to the primary mandrel 2a along the tubular device 8. Finally, in location A3, i.e., with the dispenser 56 and conductor 58 outside the generally circular path of the horn gears 72, e.g., outside the path 78 shown in FIG. 4B, or otherwise directed towards the primary mandrel 2a after the braiding operation, all of the reinforcement members 6 may only surround the primary mandrel 2a and the conductor 58 may remain outside all of the reinforcement members 6, e.g., closest to the outer surface of the tubular device 8 shown in FIG. 4C.

Optionally, if desired, individual carriers may be loaded with multiple reinforcement members (not shown), e.g., such that multiple reinforcement members are braided adjacent one another in each direction from each carrier. For example, with the conductor 58 directed from location A1 (also called the "triaxial" location), a first set of reinforcement members 43a may travel and be braided in a first direction by the horn gears 72 such that all of the windings of the first set 43a pass between the conductor 58 and the primary mandrel 2a at that specific horn gear. A second set of reinforcement members 43b may travel and be braided in a second opposite direction by the horn gears 72 such that all of the windings of the second set 43b pass over the conductor 58 at that specific horn gear. Otherwise, the reinforcement members may pass over and under one another according to the arrangement of horn gears 72 and carriers 74 loaded onto the reinforcement source 70, which pattern generally alternates at each subsequent horn gear, e.g., as described in U.S. Publication No. 2014/0323964, incorporated by reference herein.

With further reference to FIG. 4A, as can be seen, the primary mandrel 2a may exit the guide 60 with the liner material 4a being wrapped substantially around the primary mandrel 2a. With the conductor 58 directed from the desired location, the conductor 58 may be directed towards the primary mandrel 2a such that the conductor 58 is braided around the primary mandrel 2a with the reinforcement members 6 (location A4), or may extend longitudinally along the primary mandrel 2a and yet be disposed adjacent the primary mandrel 2a before braiding (location A2), braided into the reinforcement members 6 (location A1), or after braiding (location A3).

At any time, the dispenser 56 may be moved to a different location than its current one to transition the conductor 58 to the desired position relative to the primary mandrel 2a and/or reinforcement members 6. This transition may be performed substantially continuously, e.g., by directing the dispenser 56 to the desired location after a predetermined length or portion of the tubular device 7 has been braided in the desired manner. Alternatively, discrete lengths or portions may be braided in the desired manner, e.g., by stopping the apparatus 50, removing and repositioning the dispenser 56 to position the conductor 58 to the desired position relative to the primary mandrel 2a and/or reinforcement members 6, and then resuming operation for a desired time and/or length. This process may be repeated as many times as desired, e.g., to produce tubular devices, such as those described elsewhere herein.

Figure 5A:
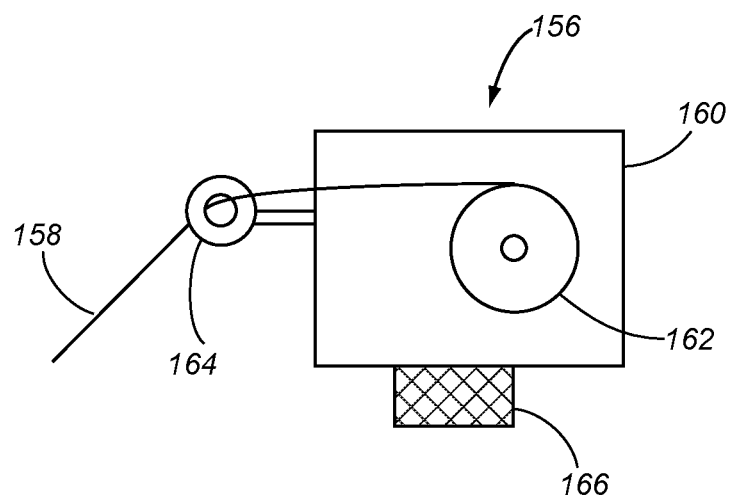
FIGS. 5A and 5B show exemplary embodiments of conductor dispensers that may be included in the braiding apparatus of FIGS. 4A and 4B.
Figure 5B:
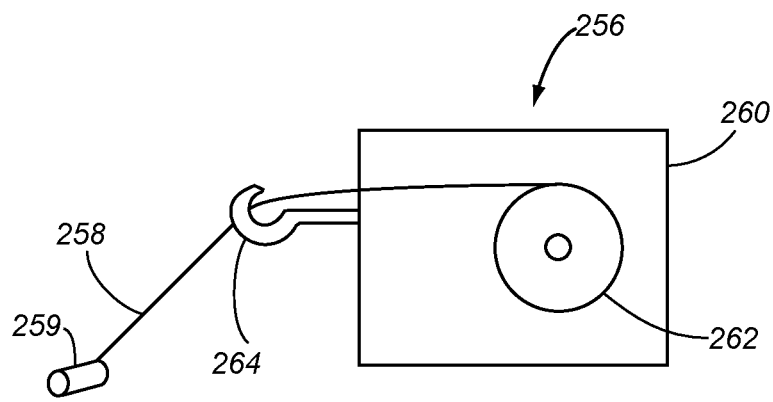

Turning to FIGS. 5A and 5B, exemplary embodiments of dispensers 156, 256 are shown that may be provided at the desired location(s) relative to the apparatus 50 of FIGS. 4A and 4B. For example, the dispenser 156 shown in FIG. 5A generally includes a housing 160 carrying a spool 162 that includes a tension mechanism (not shown), and a guide, e.g., eyelet 164, for guiding conductor 158 from the spool 162. Optionally, one or more additional guides and/or tensioners (not shown) may be provided on the dispenser 156 and/or between the dispenser 156 and other components of the apparatus 50, e.g., to guide the conductor 158 into the desired position and/or ensure that the conductor 158 is sufficiently taught as it is directed towards the primary mandrel 2a.

In addition, the housing 160 may include one or more fasteners, couplings, and/or attachment mechanisms 166 for securing the dispenser 156 at a desired location, such as one or more screws, bolts, or other fasteners, magnets, latches, snap connectors, and the like (not shown). Thus, the dispenser 156 may be mounted at a desired location, conductor 158 delivered from the spool 162, and then moved to another location one or more times, as desired, to position the conductor 158 in the desired position and/or configuration relative to the primary mandrel 2a. In one embodiment (not shown), the dispenser 156 may mount alongside, e.g., on the same axle as, a spool carrying one or more reinforcement members 6 and may utilize the same tensioning mechanism, guides, etc. or incorporate independent tensioning mechanisms(s), guides, etc.

The length of conductor 158 carried by the dispenser 156 may be sufficient for multiple tubular devices, e.g., delivered in a substantially continuous manner, or for a single tubular device, as desired. FIG. 5B shows an alternative embodiment of a dispenser 256 that includes a housing 260 carrying a spool 262 and guide 264, which may be generally similar to the dispenser 156. However, in this alternative, an electrode 259 is included pre-attached on a first or free end of the conductor 258 (with the second end wound on the spool 262). The length of the conductor 258 provided on the spool 262 may be sufficient for a single tubular device, e.g., such that the electrode 259 may be mounted on the primary mandrel (not shown) corresponding to a distal portion of a tubular device, and then the conductor 258 may be delivered from the spool 262 to position the conductor on or around the primary mandrel, as desired, e.g., similar to the apparatus 110 shown in FIGS. 3A and 3B.

For example, for the apparatus 110, a conductor 145 may be braided helically in a proximal direction from a first (e.g., distal-most) electrode 148 mounted on the reinforcement layer 142. A second electrode 148 may be positioned on the reinforcement layer 142 proximal to the first electrode 148 and a second conductor 145 braided helically from the second electrode 148 (e.g., from another dispenser similar to dispenser 256 in FIG. 5B) along with the first conductor 145. This process may be repeated, as desired, to provide a desired number of electrodes 148 and conductors 145, e.g., three as shown in FIGS. 3A and 3B.

Once all the desired conductors 145 and electrodes 148 are placed, braiding may be continued proximally, e.g., until the portion of the braided catheter where the wires either need to exit for attachment to other electrical elements or the catheter is otherwise protected from bending (e.g., which may cause path length changes capable of damaging, fatiguing, breaking, or otherwise affecting the conductors). In an exemplary embodiment, at a desired location corresponding to the desired exit of each conductor, e.g., adjacent the proximal end, the dispenser(s) may be moved from the A4 (braiding) location to the A3 location such that the conductor(s) are placed outside the braid circle for the remainder of the shaft braiding. In some instances, it may be helpful to have the conductor(s) re-enter the catheter before termination at the proximal end whether inside or outside of the hub or handle. This embodiment may provide one or more advantages, e.g., relatively low profile, ease of manufacture, protection of the conductor, access to the conductor where needed, flexing of the conductor, providing a braid construction that is substantially homogeneous, and the like as described elsewhere herein.

Figure 6A:
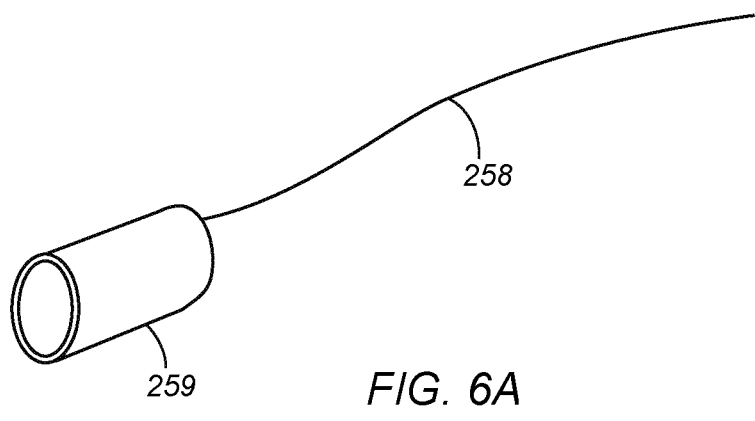
FIGS. 6A-6C are details showing exemplary embodiments of electrode components that may be included in a tubular device.
Figure 6B:
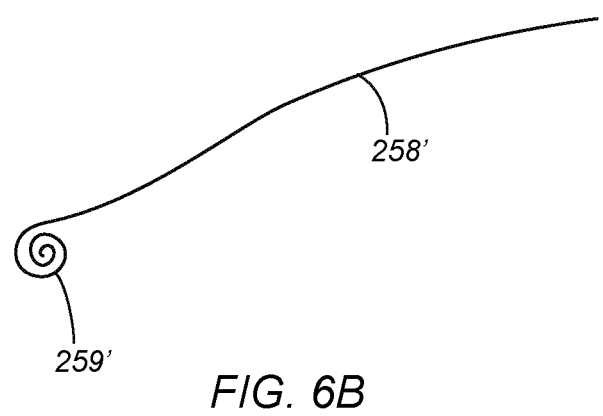
Figure 6C:
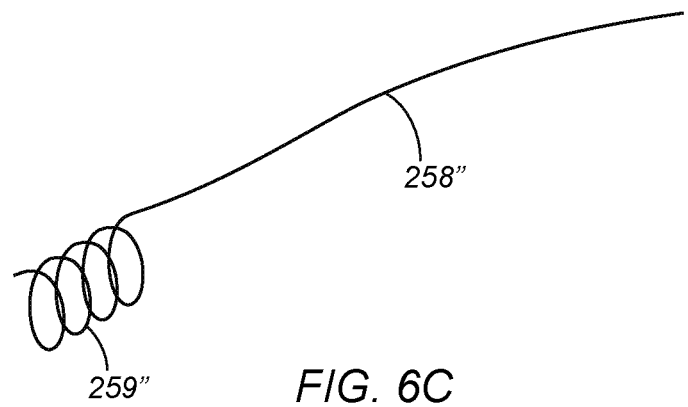

FIGS. 6A-6C show alternative embodiments of electrodes that may be provided pre-attached to a conductor and carried by a dispenser, such as that shown in FIG. 5B. For example, FIG. 6A shows a conductor 258 and electrode 259 similar to that shown in FIG. 5B, i.e., with a tubular electrode 259 attached to the conductor 258, e.g., by welding, soldering, fusing, bonding with adhesive, and the like. In an alternative embodiment, the electrode(s) may be formed from a portion of the conductor itself, e.g., formed into a desired shape or form, e.g., with desired portion(s) of the conductor removed.

For example, FIG. 6B shows an electrode 259' in the form of a round spiral sensor, e.g., formed by coiling an end of the conductor 258' into a planar or approximately planar spiral or into a partially cylindrical shape to wrap around a portion of a tubular body. The planar spiral electrode may be attached over the braid or the outer jacket, as desired, e.g., by bonding with adhesive, embedding, and the like.

FIG. 6C shows another embodiment electrode 259" in the form of an annular coil, which may be wrapped or otherwise positioned around the apparatus (not shown). For example, the conductor 258" may be wrapped one or more times, e.g., multiple times, around a tubular device outside the braid, e.g., before or after applying the outer jacket, until a coil of a desired length is formed. In the embodiments of FIGS. 6B and 6C, the insulation may be removed from the outer, exposed surfaces of the resulting coil, e.g., leaving the inner surfaces covered with insulation to avoid electrical contact with reinforcement elements of the braid, which may be conductive or semi-conductive.

Returning to FIGS. 4A and 4B, the drive mechanism 80 may include one or more components for pulling or otherwise directing the mandrels 2 through the apparatus 50. For example, the drive mechanism 80 may include a pair of spaced-apart rollers 82 coupled to a motor (not shown) that engage the reinforcement-wrapped mandrels 2 and apply sufficient tension to pull the mandrels 2 from their sources 52 through the guide 60 and/or horn gear 72a while the reinforcement members 6 are braided around the mandrels 2. Alternatively, the drive mechanism may be provided before the reinforcement members 6 are braided around the mandrels 2, e.g., pushing the primary mandrel 2a through the braiding operation and potentially pulling the auxiliary mandrel 2b by the braiding action itself. Optionally, other drive mechanisms and/or tension adjusters (not shown) may be provided for maintaining a desired tension and/or otherwise guiding the mandrels 2, liners 4, reinforcement members 6, and assembled device in a desired manner along the fabrication path.

Optionally, as shown in FIG. 4A, the jacket source 90 may be provided for applying one or more layers of jacket material around the reinforcement-wrapped mandrels 2. For example, a co-extruder, laminator, or other applicator may be provided that applies melted, uncured, and/or otherwise raw jacket material 7, e.g., from a hopper or other container (not shown), or rolls sheets of jacket material 7 may be wrapped around the reinforcement members 43 and mandrels 2. For example, for thermoplastic or other flowable materials, a heater (not shown) within a co-extruder may melt or otherwise soften the jacket material 7 to allow the jacket material 7 to flow around the reinforcement members 43 and into contact with the liner material 4 surrounding the mandrels 2 (or the mandrels 2 directly if no liner material is provided). Alternatively, the jacket material 7 may be a thermoset plastic or other material such that components of the jacket material 7 may be delivered into the co-extruder, e.g., as a liquid, powder, and the like, and mixed to form a slurry that is delivered around the reinforcement-wrapped mandrels 2. The components may chemically or otherwise react with one another and/or be heat fused to form a solid jacket 7 once cured. Exemplary materials for the jacket material 7 include plastics, e.g., thermoplastics, such as polyether block amide, nylon, or urethanes, thermoset plastics, metals, or composite materials. Alternatively, other processing may be used to bond or otherwise attach the jacket material 7 to the liner material 4 and/or embed the reinforcement members 43 in the jacket material 7, thereby resulting in an integral tubular body 8.

The resulting tubular body 8 (with or without jacket material 7) may be collected, e.g., on a capture reel or in a container (not shown). Thereafter, the tubular body 8 may be further processed to make a catheter, sheath, or other device. For example, a cutter or other tool (not shown) may separate the tubular body 8 into individual tubular shafts, e.g., before or after removing the mandrels 2. For example, the mandrels 2 may remain within the tubular body 8 when cut into individual devices, and then may be removed, resulting in a primary lumen, e.g., similar to the apparatus 10 shown in FIG. 1B. Alternatively, if the friction between the mandrels 2 and the surrounding material is relatively low, the mandrels 2 may be removed before the tubular body 8 is cut into individual devices.

The resulting inner surface 41a of the primary lumen 18a may have a substantially uniform cross-section, e.g., as shown in FIG. 1B. Similar the auxiliary lumen 18b may also have a substantially uniform cross-section, e.g., also as shown in FIG. 1B or may have a variable cross-section, if desired (not shown).

Other components may be added to the individual tubular devices, as desired for the particular application. For example, for a steerable catheter, such as the apparatus 10 shown in FIGS. 2A and 2B, a steering element 36 may be inserted through the auxiliary lumen 18b (created when the auxiliary mandrel 2b is removed). In an alternative embodiment, the auxiliary mandrel 2b may remain within the tubular device to provide the steering element, e.g., if the friction between the outer surface of the auxiliary mandrel 2b and the liner or other material defining the auxiliary lumen is relatively low. A tip or other component (not shown) may be attached to a distal end 14 of the apparatus 10, e.g., after attaching the distal end 36b of the steering element 36 to the tip. The other end of the steering element may be coupled to an actuator 34 of a handle 30 attached to a proximal end 12 of the apparatus 10, e.g., similar to the embodiment shown in FIG. 1A and described elsewhere herein.

In alternative embodiments, one or more electrodes may be embedded within the apparatus, rather than electrically exposed on an outer surface of the apparatus. For example, where the primary purpose of the electrode(s) is to generate or sense an electric or magnetic field (as opposed to a conductive interface necessary for some measurements), the outer jacket may be positioned over the conductors/electrodes (not shown). If the outer jacket is not substantially electrically conductive, but instead permits the passage of electric or magnetic fields, the apparatus may allow transmission and/or sensing of electric or magnetic fields via the embedded electrodes without direct contact with the tissue.

Such a construction may provide one or more advantages, e.g., in one or both of construction and performance. For example, with regards to performance, there may be no chemical interaction between the embedded electrode and tissue adjacent the apparatus, which may be used to reduce potential complications or may enable the use of alternative materials that might otherwise not be ideal or compatible for its use or interaction with tissue (for example, a simple copper electrode may be used instead of gold or platinum) since the materials are isolated from any direct contact with tissue or bodily fluids.

From a construction standpoint, the ability to embed electrodes beneath the surface of the outer jacket may simplify construction and/or may enable alternative constructions that make assembly (including various orders of operations) easier. For example, electrodes are frequently attached externally using a number of labor-intensive and sometimes complicated operations. Sometimes swaging is used to mechanically embed the electrodes into the wall of the catheter. This embeds the edges of the electrode into the jacket making the electrode atraumatic and stable; however it may have a damaging effect on the continuity of the catheter in terms of inner profile, or torque/kink resistance/continuity.

In many other instances, the electrodes are bonded to the catheter using adhesives. In these instances, the same or secondary adhesive is used to create a "ramp" or "fillet" to cover the edge of the electrode to prevent it from causing damage to body tissues, etc. In the case of embedded electrodes, the electrodes may be placed on the catheter before applying the jacket material(s) and/or subsequent lamination. The lamination of the catheter (a step that is done regardless of the presence of electrodes) may automatically fix the position of the electrodes and/or cover the electrode edges, and may do so with minimal impact to the catheter performance in terms of profile, kink/torque performance, and the like.

Embedding the electrode(s) may also simplify the construction and maintenance of electrical isolation from other electrodes. The electrodes may be insulated before or at the time of their placement into the catheter. For example, an insulator, such as polyimide, parylene, and the like may be used to cover the electrode(s) with a thin, insulating barrier such that the electrode(s) cannot be accidentally placed in electrical connection with other electrodes and/or with other elements of the catheter such as reinforcement members, e.g., the electrode inner surface may be electrically insulated.

In an alternative embodiment, the embedded electrode(s) may be made electrically conductive to the environment outside of the catheter by one or more methods. For example, one or more holes or passages may be cut, drilled, laser ablated, achieved by solvent removal, and/or otherwise created through the overlying jacket material to expose at least a portion of the embedded electrode. Alternatively or in addition, the overlying jacket may be made locally electrically conductive, e.g., by doping and the like.

Further alternatively, the shape or profile of the embedded electrode may be such that at least a portion of the embedded electrode is disposed nearer to, at, or above the surface of the catheter, e.g., including one or more bumps, knobs, ridges, projections, and the like, e.g., to cause the portion to be exposed during lamination of the catheter shaft or more easily exposed after lamination of the catheter shaft.

In additional alternative embodiments, in addition to or instead of wires or conductors, other elongate members may be braided and/or otherwise incorporated into a tubular device, such as one or more fiberoptic bundles, tensile elements, capillary tubing, and/or stiffening elements. For example, a coherent or non-coherent imaging fiber may be provided within a wall of an imaging catheter, illumination catheter, and/or other tubular devices that include one or more sensors of various types (including diffraction gratings for stress strain measurements and the associated calibrations for force or position). The position and/or configuration, e.g., whether braided or longitudinal, may be selected along one or more portions of the tubular device, as desired.

Figure 7A:
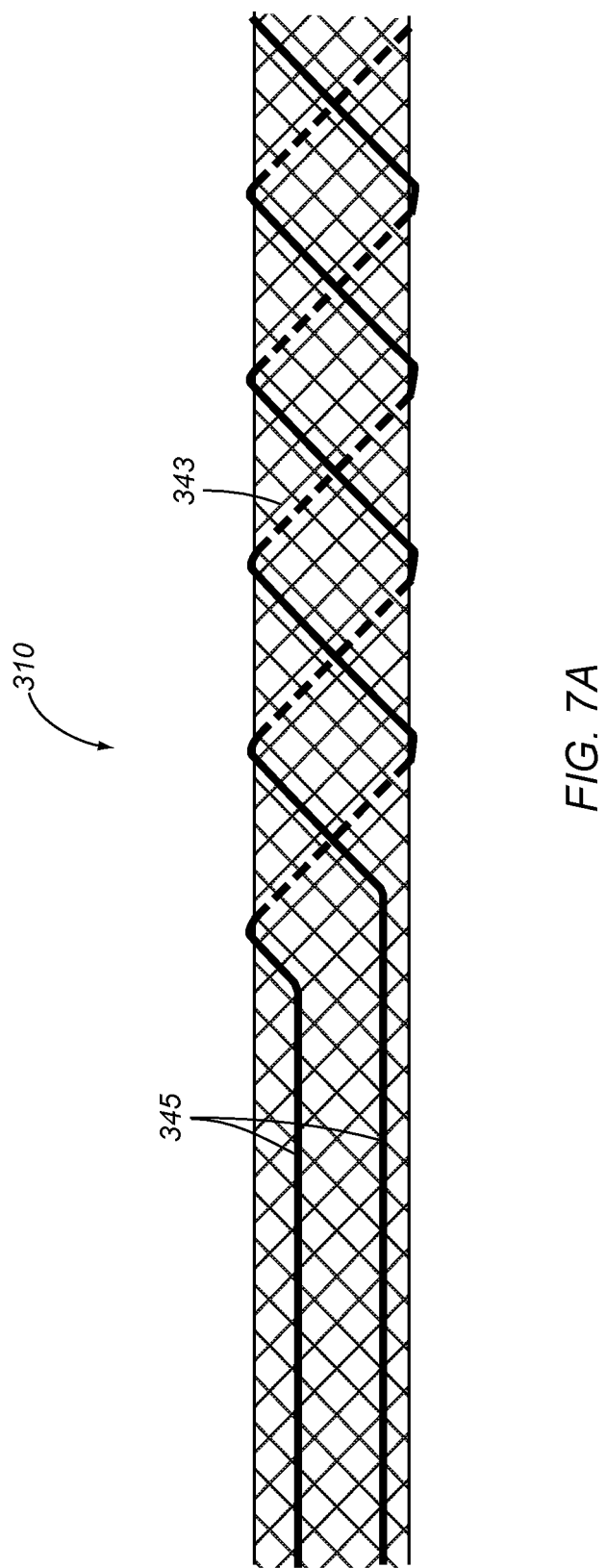
FIGS. 7A and 7B are details showing exemplary configurations for incorporating conductors into a tubular device.

Turning to FIG. 7A, in another embodiment, elongate stiffening elements may be provided within an apparatus 310 instead of or in addition to one or more conductors (not shown). For example, as shown, a pair of stiffening elements 345 may be provided that extend substantially longitudinally generally opposite one another along a first portion and then transition to a helical, braided configuration, e.g., along with one or more reinforcement members 343, as shown. In this embodiment, the stiffening or stabilizing element(s) 345 (e.g., pre-loaded onto a dispenser, not shown) may be located at one of the A1, A2, or A3 locations in FIGS. 4A-4C, thereby positioning the stiffening element(s) 345 substantially longitudinally along one or more portions where lateral or other stabilization is desired. Outside of such portion(s), where the catheter is desired to again have rotationally homogenous properties, the stiffening/stabilization element(s) 345 may be transitioned to the A4 location, e.g., braiding along with one or more reinforcement members 343.

For example, two stiffening elements 345 may be provided about one hundred eighty degrees opposite each other, e.g., in the A1 location along a strategic portion (for example in a deflectable catheter, or in a shape set catheter). The stiffening elements 345 may resist compression and/or extension and limit flexing in a single plane. This plane may be used for the shape/form setting or the deflection plane, e.g., along a steerable or deflectable distal portion. Proximal to such a distal portion, another portion of the catheter (e.g., the intermediate and/or proximal portion may become smoothly torqueable by braiding the stiffening elements 345 substantially helically with the reinforcement members and their stiffening effect may be substantially neutralized.

Figure 7B:
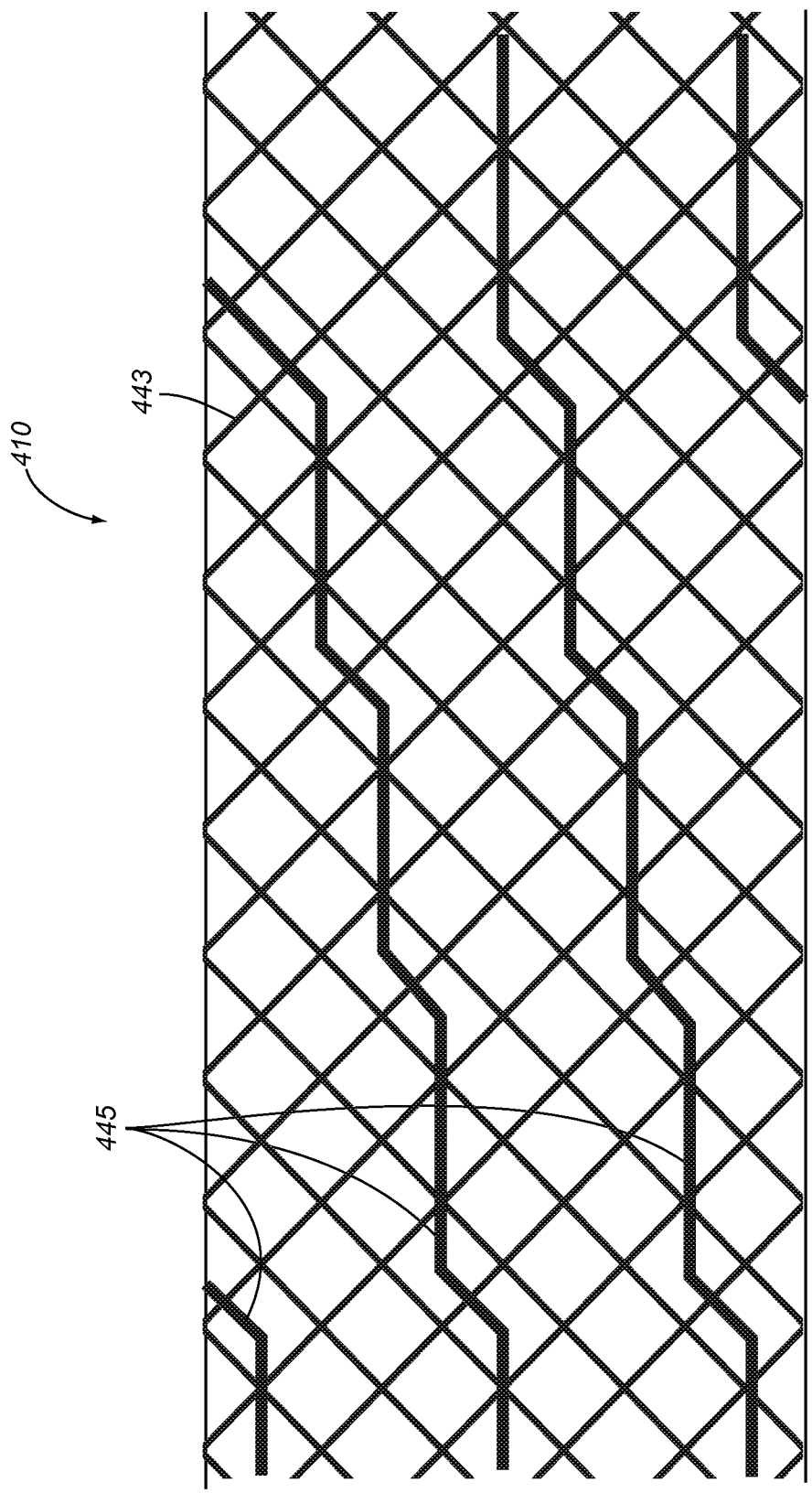

Optionally, more complicated configurations may be provided for elongate components within a tubular device. For example, FIG. 7B shows an exemplary embodiment of an apparatus 410 that includes a plurality of stiffening elements 445 that are transitioned multiple times between a braided, helical configuration, and a longitudinal configuration. Such a repeated helical/longitudinal construction may provide a tubular device having a desired bend profile, e.g., such that the tubular device bends in a helical manner, rather than within a plane.

Additionally, the elements may be tensile elements that are otherwise limp, such as rope, string, braided fibers, fibers (e.g., Kevlar), or other polymeric elements (e.g., UHMWPE). Such elements may create regions of increased tensile strength, elongation resistance (but keeping flexibility) or areas of stiffness complemented by areas of flexibility. The specific angular position of the tensile or stiffening element(s) may vary along the length to create complex bend profiles, or complex support profiles, etc. For example, as shown in FIG. 7B, three tensile elements 445 are provided that are located about one hundred twenty degrees (120°) from each other about the circumference of the apparatus 410. In the longitudinal configuration (e.g., with the dispenser(s) at the A1 location), the apparatus 410 may be substantially inflexible in all planes, while in another region, the stiffness may be transitioned such that the resulting stiffness resists motion except in one plane.

The foregoing disclosure of the exemplary embodiments has been presented for purposes of illustration and description. It is not intended to be exhaustive or to limit the invention to the precise forms disclosed. Many variations and modifications of the embodiments described herein will be apparent to one of ordinary skill in the art in light of the above disclosure.

Further, in describing representative embodiments, the specification may have presented the method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. A tubular device for a catheter or sheath comprising a proximal end and a distal end sized for introduction into a patient's body, the tubular device comprising:
   a central lumen extending between the proximal and distal ends, thereby defining a longitudinal axis;
   an elongate conductor extending at least partially between the proximal and distal ends adjacent the central lumen;
   one or more reinforcement members comprising windings extending helically around the central lumen between the proximal and distal ends; and
   an outer jacket surrounding the one or more reinforcement members,
   wherein the tubular device comprises a first portion in which the conductor and the reinforcement members extend helically around the central lumen, and a second portion in which the reinforcement members extend helically around the central lumen and the conductor extends substantially parallel to the longitudinal axis and either a) all of the windings surround the central lumen and the conductor remains outside the windings, b) at least some of the windings pass between the central lumen and the conductor and at least some of the windings surround both the central lumen and the conductor, and c) all of the windings surround both the central lumen and the conductor.

2. The tubular device of claim 1, wherein the second portion is a distal portion adjacent the distal end, and the first portion is an intermediate portion between the proximal end and the distal portion.

3. The tubular device of claim 2, further comprising one or more sensing elements carried on the distal portion and coupled to the conductor.

4. The tubular device of claim 2, wherein the conductor comprises a plurality of wires, the tubular device further comprising a plurality of sensing elements carried on the distal portion and coupled to respective wires of the plurality of wires.

5. The tubular device of claim 2, wherein the plurality of wires are braided around the central lumen in the same direction immediately adjacent one another along the first portion.

6. The tubular device of claim 2, further comprising a steering element extending between the proximal and distal ends, the steering element extending along the distal portion within an auxiliary lumen, the auxiliary lumen extending substantially parallel to the longitudinal axis along the distal portion offset about ninety degrees around a circumference of the distal portion relative to the conductor.

7. The tubular device of claim 1, wherein the conductor exits through the outer jacket at a location adjacent the second portion.

8. The tubular device of claim 7, wherein the second portion comprises a proximal portion adjacent the proximal end, the tubular device further comprising a handle on the proximal end including a connector, wherein the conductor is coupled to the connector.

9. The tubular device of claim 1, wherein the tubular device further comprises a third portion adjacent the second portion in which the conductor extends helically around the central lumen.

10. The tubular device of claim 1, wherein the tubular device further comprises a third portion adjacent the first portion opposite the second portion in which the conductor extends substantially parallel to the longitudinal axis and either a) all of the windings surround the central lumen and the conductor remains outside the windings, b) at least some of the windings pass between the central lumen and the conductor and at least some of the windings surround both the central lumen and the conductor, and c) all of the windings surround both the central lumen and the conductor.

11. The tubular device of claim 1, wherein the conductor comprises a plurality of wires that are braided around the central lumen in the same direction immediately adjacent one another along the first portion.

12. The tubular device of claim 1, wherein the wires exit through the outer jacket adjacent the second portion.

13. The tubular device of claim 12, wherein the wires exit through the outer jacket at different axial locations along the second portion.

14. The tubular device of claim 1, wherein, along the second portion, all of the windings surround the central lumen and the conductor is disposed outside the windings.

15. The tubular device of claim 1, wherein, along the second portion, at least some of the windings pass between the central lumen and the conductor and at least some of the windings surround both the central lumen and the conductor.

16. The tubular device of claim 1, wherein, along the second portion, all of the windings surround both the central lumen and the conductor.

17. The tubular device of claim 1, wherein, along the first portion, the conductor is braided with the reinforcement members.

18. The tubular device of claim 17, wherein the conductor is braided with the reinforcement members such that the conductor extends helically around the central lumen in the same direction immediately adjacent one of the reinforcement members.

19. A tubular device for a catheter or sheath comprising a proximal end and a distal end sized for introduction into a patient's body, the tubular device comprising:
    a central lumen extending between the proximal and distal ends, thereby defining a longitudinal axis;
    one or more reinforcement members comprising windings extending helically around the central lumen between the proximal and distal ends;
    an outer jacket surrounding the one or more reinforcement members;
    a conductor extending at least partially between the proximal and distal ends adjacent the central lumen; and
    a steering element extending between the proximal and distal ends within an auxiliary lumen,
    wherein the tubular device comprises a steerable distal portion adjacent the distal end in which the conductor and steering element extend substantially parallel to the longitudinal axis with the auxiliary lumen offset about ninety degrees around a circumference of the distal portion relative to the conductor, and
    wherein the tubular device comprises an intermediate portion proximal to the distal portion in which the conductor extends helically around the central lumen and is braided with the reinforcement members.

20. The tubular device of claim 19, wherein the one or more reinforcement members comprise windings extending helically along the distal portion.

21. A tubular device for a catheter or sheath comprising a proximal end and a distal end sized for introduction into a patient's body, the tubular device comprising:
    a central lumen extending between the proximal and distal ends, thereby defining a longitudinal axis;
    one or more reinforcement members comprising windings extending helically around the central lumen between the proximal and distal ends;
    an outer jacket surrounding the one or more reinforcement members; and
    a plurality of conductors extending at least partially between the proximal and distal ends adjacent the central lumen;
    wherein the tubular device comprises a distal portion adjacent the distal end in which the reinforcement members extend helically around the central lumen and the plurality of conductors extend substantially parallel to the longitudinal axis, the distal portion comprising a plurality of sensing elements spaced apart from one another along a length of the distal portion, each sensing element coupled to at least one of the conductors, and
    wherein the tubular device comprises an intermediate portion proximal to the distal portion in which the conductors extend helically around the central lumen and are braided with the reinforcement members.

\* \* \* \* \*